United States Patent [19]

Kubela et al.

[11] 4,080,330

[45] Mar. 21, 1978

[54] PHENYLINDOLINES AND PROCESS FOR THEIR PRODUCTION

[75] Inventors: Rudolf Kubela, Cote St. Luc; Vaclav Musil; Lise A. Hughes, both of Ville-de-Lery, all of Canada

[73] Assignee: Delmar Chemicals Limited, Ville la Salle, Canada

[21] Appl. No.: 589,402

[22] Filed: Jun. 23, 1975

[51] Int. Cl.$^2$ .............................................. C07D 209/4
[52] U.S. Cl. .................... 260/326.11 R; 260/268 BC; 260/293.61; 260/295 B; 260/296 A; 260/319.1; 260/326.16; 424/267; 424/274; 424/248.54; 544/143; 544/144; 424/263
[58] Field of Search ................ 260/326.1 R, 247.2 A, 260/268 BC, 293.61, 326.11 R; 424/274

[56] References Cited

U.S. PATENT DOCUMENTS

| 3,184,466 | 5/1965 | Hennig et al. ............. 260/326.11 R |
| 3,558,653 | 1/1971 | Coyne et al. ..................... 260/326.11 |
| 3,644,403 | 2/1972 | Canas-Rodriguez et al. ... 260/326.11 |
| 3,890,348 | 6/1975 | Kathawala ................. 260/326.11 R |

FOREIGN PATENT DOCUMENTS 43-3614  2/1968  Japan .......................... 260/326.11 R

*Primary Examiner*—Ethel G. Love
*Attorney, Agent, or Firm*—Virgil H. Marsh

[57] ABSTRACT

The present invention is concerned with novel 2-unsubstituted-3-phenylindolines and acid addition salts thereof. These compounds have been found to have valuable pharmacological properties indicative of possible utility, inter alia, of controlling coagulation of the blood and as hypoglycemic agents. The invention also provides novel processes for producing the novel compounds and pharmaceutical compositions containing same as active ingredients.

6 Claims, No Drawings

PHENYLINDOLINES AND PROCESS FOR THEIR PRODUCTION

FIELD OF INVENTION

The present invention relates to novel substituted and unsubstituted 3-phenylindolines, processes for the production thereof and pharmaceutical compositions containing such compounds as active ingredient.

BACKGROUND OF INVENTION

Certain 3-substituted indolines are known in the art, and various methods have been employed for their preparation. Furthermore, whilst some 3-phenyl indolines are known, to the best of our knowledge, all such compounds are either simultaneously substituted in the 2-position and/or carry an additional substituent in the 3-position. The indolines of the present invention are characterized by being unsubstituted in the 2-position and substituted only by a phenyl residue in the 3-position.

SUMMARY OF INVENTION

The present invention in a composition of matter aspect provides novel 2-unsubstituted-3-phenylindolines which may also be 1- (i.e. N-) substituted by various residues including alkyl and acyl residues. Also within the scope of this invention are the non-toxic acid addition salts of the novel 3-phenyl indolines which contain basic nitrogen. The present invention also provides a process for the preparation of the novel 3-phenylindolines which process involves the direct reduction under selected conditions of a 3-phenylindole. It has been found that the compounds of the present invention possess valuable properties, as indicated by standard pharmacological tests with animals, indicative of possible use inter alia in controlling coagulation of the blood, as a local anaesthetic, intestinal relaxant, antihistaminic and hypoglycemic agent generally with an acceptable toxicity level.

DETAILED DESCRIPTION OF INVENTION

The present invention provides novel 3-phenylindolines of the general formula I:

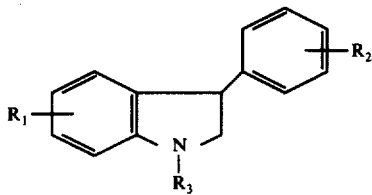

I wherein $R_1$ and $R_2$ individually represents hydrogen, halogen, lower alkoxy or lower alkyl; $R_1$ being in the 5—, 6— or 7— position only; $R_3$ represents (a) hydrogen;

(b) a moiety of formula

wherein $R_4$ is amino; amino mono-substituted by lower alkyl, phenyl or substituted phenyl; straight or branched chain lower alkenyl; straight or branched chain lower alkyl optionally substituted by halogen, azido, alkanoyl or aminoalkyl of formula

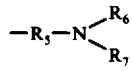

wherein $R_5$ is a straight or branched chain lower alkyl group;

$R_6$ and $R_7$ individually represent hydrogen; lower alkyl; pyridyl; phenyl; or phenyl substituted by one or more lower alkyl groups or halogen atoms; or $R_6$ and $R_7$ together with the nitrogen and, optionally an oxygen or further nitrogen, represent a heterocyclic ring containing 5, 6 or 7 ring members, any further nitrogen atom optionally carrying a lower alkyl; or (c) a moiety of formula

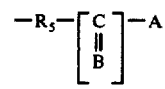

wherein

represents —CH$_2$—; or

and A represents an amino group of formula

wherein $R_5$, $R_6$ and $R_7$ are as defined above, and pharmaceutically acceptable addition salts thereof with inorganic or organic acids.

It will be noted that the compounds of formula I above have an assymetric centre at $C_3$ and these compounds may therefore exist as optical isomers. The connotation of the general formulae presented herein is to include all such isomers either separated or in racemic mixtures, the latter being indicated throughout the text unless otherwise specified.

The term "halogen" as used throughout the present specification refers to fluorine, chlorine or bromine, especially chlorine and fluorine. The term "lower" when used throughout this specification to qualify organic groups, means such groups having at most six, preferably at most four, and especially one or two, carbon atoms. Examples of lower alkyl groups include methyl, ethyl, propyl, isopropyl, butyl, isobutyl secondary and tertiary butyl and the various pentyl and hexyl isomers. Examples of lower alkenyl are vinyl, 1-propenyl, 2-propenyl (vinyl), 1-isobutenyl and 1-hexenyl. Non-cyclic amino residues represented by —NR$_6$R$_7$ include amino, methylamino, dimethylamino, ethylamino, propylamino, isopropylamino, butylamino, isobutylamino, pentylamino, isopentylamino and hexylamino; also, phenylamino; (1'-methylphenyl)amino;

(1',6'-dimethylphenyl)amino; (1'-chlorophenyl)amino; (1',6'-dichlorophenyl)amino; and piperidinylamino.

Cyclic amino residues represented by —NR₆R₇ i.e., when —NR₆R₇ is a heterocyclic ring, include pyrrolidinyl; piperidinyl; piperazinyl, which may be substituted by lower alkyl on the 4-nitrogen; and morpholino.

The novel 3-phenylindolines of the present invention are prepared by reduction of suitable 3-phenylindoles.

In general only the N-unsubstituted 3-phenylindolines are prepared by reduction of the corresponding indole; the N-substituted compounds of formula I being obtained from the N-unsubstituted indolines of formula I.

According to a process aspect of the present invention compounds of the formula I*a*:

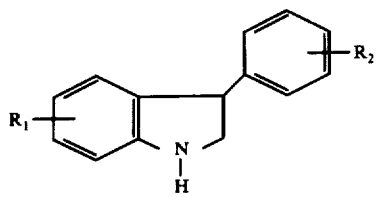

wherein $R_1$ and $R_2$ are as defined above for formula I are prepared by reducing in a strongly acid medium a 3-phenylindole of formula II:

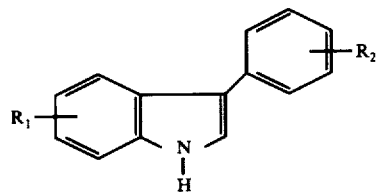

wherein $R_1$ and $R_2$ are as defined above for formula I.

The required conditions may be conveniently provided by effecting the reaction in the presence of a strong protonating agent, such mineral acids, for example, as hydrochloric acid, hydrofluoroboric acid or σ-phosphoric acid, or Lewis acids, such as borontrifluoride, aluminium trichloride and zinc dichloride in the presence of an organic acid, such as glacial acetic acid, propionic acid, trifluoroacetic acid and formic acid being suitable.

Reduction of the indole to the corresponding indoline may be effected catalytically utilizing a hydrogenation procedure in the presence of a suitable catalyst, such as platinum or palladium. Examples of such reducing systems include hydrofluoroboric acid/platinum oxide and hydrofluoroboric acid/palladium-charcoal in lower alcohols as solvent.

Alternatively, a strongly acidic chemical reducing system may be used, examples thereof being boron trifluoride/zinc dust/glacial acetic acid and zinc dust/hydrochloric acid.

The N-substituted compounds of formula I are conveniently prepared using the unsubstituted compounds of formula I*a* as the starting materials. For example, the compounds of restricted formula I*b*:

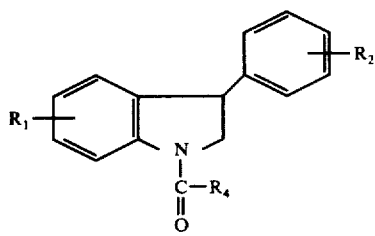

wherein $R_1$, $R_2$ and $R_4$ are as defined above for formula I, may be prepared by reacting a 3-phenylindoline of formula I*a* above with a reactive derivative of formula III:

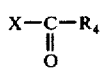

wherein X is a reactive moiety such as hydroxy; halogen; preferably chlorine; or an ether residue, if necessary in the presence of a suitable catalyst. For example, an ester reactant of formula III would generally be used in combination with a condensing agent such as a carbodiimide, for example, N,N'-dicyclohexyl carbodiimide.

Alternatively, one compound of formula I*b* may be obtained from another compound of formula I*b*. For example, compounds wherein $R_4$ is a halogenoalkyl moiety, (the residue

having been introduced into the molecule in the manner described immediately above) may be reacted with an alkali metal azide or an amine of formula

(wherein $R_6$ and $R_7$ are as defined above for formula I) to form the corresponding azido—, or amino— alkylene compounds respectively.

Moreover, such compounds may themselves be used as starting materials in the production of further compounds of formula I*b*. For example, such azido compounds may be converted into the corresponding primary amino compound by reduction in known manner. Primary and secondary amines of formula I whether prepared in one or more steps, may, if desired, be further alkylated by known standard procedure to produce the correspondingly further alkylated compounds.

The 1-carbamoyl compounds of formula I*b* may be obtained simply by reacting the corresponding N-unsubstituted compound of formula I*a* with an inorganic, for example, alkali metal, isocyanate, such as potassium or sodium isocyanate or an organic isocyanate of formula RNCO wherein R is lower alkyl or unsubstituted or substituted phenyl; such as methyl isocyanate, ethylisocyanate, phenyl isocyanate, (1'-methylphenyl)isocyanate, 1',6'-dimethylisocyanate, 1'-chlorophenylisocyanate and 1',6'-dichlorophenylisocyanate.

In addition, reaction of the same compounds of formula I*a* with diketene produces those compounds of formula I*b* substituted in the 1- position by the acetoacetyl residue.

Compounds of restricted formula I*c*:

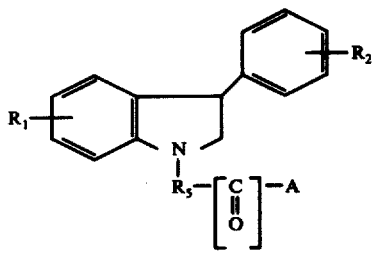

wherein $R_5$ and A are as defined above for formula I may be produced by reacting the corresponding N-unsubstituted compound of formula I*a* with a compound of formula IV:

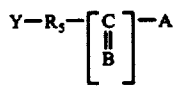

wherein Y is a labile leaving group such as halogen, especially chlorine and bromine; mesyl and tosyl;

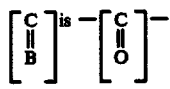

and $R_5$ and A are as defined above for formula I. The compounds of formula I*d*:

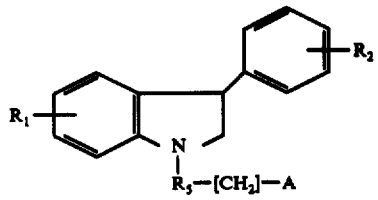

wherein $R_1$, $R_2$, $R_5$ and A are as defined for formula I*c* may be obtained from the keto compounds of formula I*c* by reduction of the

group, the reduction being effected by methods known in the art. For example, complex metal hydrides such as lithium aluminium hydride and organic hydrides such as diborane and bis(2-methoxyethoxy)aluminium hydride may be used.

Alternatively, the compounds of formula I*d* may be obtained by reacting a compound of formula I*a* with a compound of formula IV above wherein

is —[CH$_2$]— and Y, $R_5$ and A are as defined immediately above.

Additionally, when compounds of formula I wherein $R_3$ is —COR$_4$ and $R_1$ is halogen are desired, there may be obtained from the corresponding compound of formula I wherein $R_1$ is hydrogen by halogenation. For example, a 5-halogenated, such as a 5-chlorinated compound, of formula I wherein $R_3$ is —COR$_4$ may be obtained from the corresponding 5— unsubstituted compound by reaction with elemental chlorine say, chlorine in acetic acid.

As stated previously, the compounds of the present invention may exist in two isomeric forms. The processes described above produce a racemic mixture of the two possible isomers. If the mixture of isomers obtained as the product in any specific reaction is not utilizable in that form due to the undesirable presence of one isomer, the isomers may be resolved by standard techniques generally utilizing differences in the physical and/or chemical properties between the isomers, such as relative solubilities etc.

Some of the 3-arylindolines of formula I, those which are basic, form acid addition salts with various inorganic or organic acids and such salts are included within the scope of the present invention. Of special interest are the pharmaceutically acceptable acid addition salts which are usually more convenient to handle than the free compounds of formula I. Acids which form such salts include hydrochloric acid, hydrobromic acid, sulfuric acid, phosphoric acid, nitric acid, acetic acid, maleic acid, fumaric acid, tartaric acid, succinic acid, citric acid, camphorsulfonic acid, ethanesulfonic acid, ascorbic acid and lactic acid. The said salts are prepared by standard procedures usually involving treating the free base with an ethanolic solution of the desired acid, the acid addition salt being obtained generally in the form of a crystalline solid.

The starting materials, namely, the 3-phenylindoles of formula II:

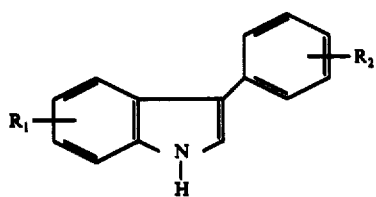

wherein $R_1$ and $R_2$ are as defined above for formula I are either known compounds or may be prepared in a similar manner to the processes for producing the known compounds. Generally, compounds of formula II may be prepared by the Fisher Indole synthesis involving the reaction of a (possibly substituted) phenyl hydrazine with an optionally substituted phenylacetaldehyde in the presence of a strong mineral or Lewis acid, such as zinc chloride, the reaction proceeding via a phenyl hydrazone intermediate as follows:

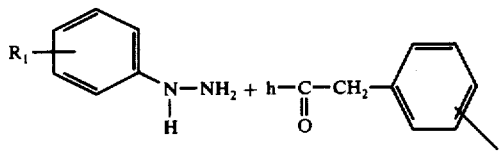

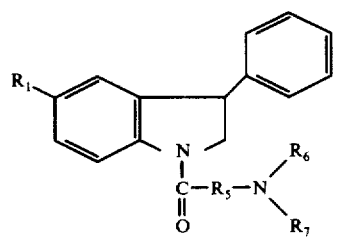

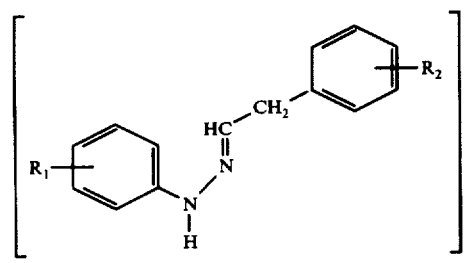

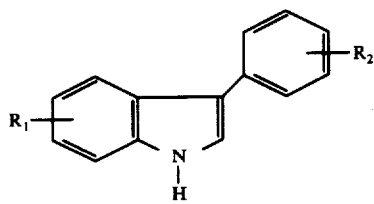

wherein R₁ and R₂ as defined above for formula I.

The starting 3-phenylindoles may also be prepared by a modification of the above process which comprises reacting an optionally substituent phenylhydrazine hydrochloride with, for example, a dimethyl or diethyl acetal of a phenylacetaldehyde in alcohol.

The various reactants required to convert the N-unsubstituted 3-phenylindolines to the corresponding N-substituted compounds, such as compounds of formula III and IV above are known compounds.

As indicated previously the novel 3-phenyl indolines of the present invention, and in particular, the N-unsubstituted compounds or those wherein the N-substituent carries a basic nitrogen atom, possess useful biological properties and generally they have activity, as determined by standard tests indicative of various possible uses. For example, many of these compounds of formula I when applied topically in standard tests using guinea pigs, have indicated possible utility as local anesthetic agents.

Also the N-unsubstituted 3-phenylindolines of restricted formula Ia, such as 3-phenylindoline itself, as well as compounds of formula Ie:

wherein
R₁ is hydrogen or halogen;
R₅ is a straight or branched chain alkylene and one of R₆ and R₇ is hydrogen and the other is lower alkyl, or both R₆ and R₇ are lower alkyl, or together with the nitrogen and an oxygen, morpholino, give strong indications via a standard platelet aggregation test evaluation (J. Lab. & Clin. Med 64, 548–559 (1964)) of utility in preventing blood clot formation.

The following table summarises the results in the said test for some of the above compounds. The results obtained in the same test for the known drugs, aspirin and adenosine were included as a comparison. Test values in excess of 50 are considered pharmacologically significant.

| Compound | Dose γ ml | Result |
|---|---|---|
| A. | | |
| 3-phenylindoline | 1 | 100 |
| N-(dimethylaminoacetyl)-3-phenylindoline | 5 | 80 |
| N-(2'-dimethylamino-2'-methylacetyl)-3-phenylindoline | 5 | 100 |
| Aspirin | 5 | 78 |
| B. | | |
| N-(2-methylamino)propionyl-3-phenyl-5-chloro-indoline | 50 | 54 |
| N-(2-methylamino)-acetyl-3-phenyl-5-chloroindoline | 100 | 78 |
| Adenosine | 100 | 78 |

Other compounds of formula I, namely those of the restricted formula If:

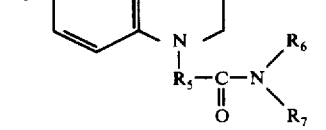

wherein
R₁ is hydrogen or halogen;
R₅ is straight or branched chain lower alkylene;
R₆ and R₇ are individually hydrogen or lower alkyl or together with the nitrogen and optionally, a further nitrogen or oxygen, represent a heterocyclic ring having 5, 6 or 7 ring members have been found to possess properties indicative of use as hypoglycemic agents. Examples of such compounds are 1-(5-chloro-3-phenyl)indolinyl acetic acid piperidid and 1-(5-chloro-3-phenyl) indolinylacetic acid dimethylanilide.

Some of the compounds have been found to have significant effect on the central nervous system indicated, as previously, by tests on experimental animals, and have properties in common with anti-depressant drugs. For example, N-(2-piperidinylethyl)-3-phenylindoline, according to the present invention and the known anti-depressant imipramine were subjected to standard test procedures for evaluating anti-depressant activity (ref. R. A. Turner, P. Hebborn, Screening Methods in Pharmacology, Vol. II, Acad. PV. N.Y., London 1971, page 214. The results obtained are shown in the following table, response values greater than three (>3) being considered pharmacologically significant.

| Compound | Dose mg/kg | Result |
|---|---|---|
| N-(2-piperidinylethyl)-3-phenylindoline | 25 | 6 |
|  | 10 | 5 |
| Imipramine | 25 | 4 |

The present invention further provides in another of its aspects a pharmaceutical composition comprising as an essential active ingredient at least one active compound of formula I or a pharmaceutically acceptable acid addition salt thereof in association with a pharmaceutically acceptable carrier therefor.

The compositions of the present invention are preferably administered orally, rectally or parenterally. Advantageously, the composition is in a dosage unit form appropriate to the desired mode of administration. For example, the dosage unit may be a tablet, capsule, pill, powder, packet, granule, wafer, elixir, suppository, or a measured quantity of a suspension, solution, a syrup or segregated multiples of the foregoing. The term "dosage units form" as used in the specification and claims refers to physically discrete units suitable as unitary dosages for human subjects and animals, each unit containing a predetermined quantity of active material calculated to produce the desired therapeutic effect in admixture, or otherwise in association, with a pharmaceutical carrier, the quantity of the active ingredient being such that one or more units are normally required for a single therapeutic administration or that, in the case of severable units such as scored tablets, at least one fraction such as a half or a quarter of a severable unit is required for a single therapeutic administration.

Usually the compositions of this invention contain the active ingredient in an amount of at least 0.5% by weight based on the total weight of the composition and not more than 95% by weight. Conveniently, the compositions of the invention when in dosage unit form contain 0.5 mg to 350 mg, and more conveniently from 5 mg to 250 mg of the active ingredient of formula I.

The compositions of the present invention will normally consist of at least one compound of formula I, advantageously a compound of the restricted forms of formula I such as formula Ia, Ib, Ie and If, or a pharmaceutically acceptable acid addition salt thereof, admixed with a carrier, or diluted by a carrier, or enclosed or encapsulated by a carrier in the form of a capsule, sachet, catchet, paper or other container. A carrier which serves as a vehicle, excipient or diluent medium for the therapeutically active ingredient may be a solid, semi-solid or a sterile liquid.

Some examples of the carriers which may be employed in the pharmaceutical compositions of the invention are lactose, dextrose, sorbitol, mannitol, starches such as wheat, corn, or potato starch, gum acacia, calcium phosphate, liquid paraffin, cocoa butter, oil of theobroma, alginates, tragacanth, gelatin, syrup B.P., methyl cellulose, polyoxethylene sorbitan monolaurate, and methyl and propyl hydroxybenzoates. The choice of carrier is determined by the preferred form of administration, the solubility of the compound and standard pharmaceutical practice, all as more clearly set forth in "Remington's Practice of Pharmacy" by E. W. Martin and E. F. Cook, a well-known reference work in this field. In the case of tablets, a lubricant may be incorporated to prevent sticking and binding of the powdered ingredients in the dies and on the punch of the tabletting machine. For such purpose, there may be employed, for example, talc, aluminum, magnesium or calcium stearates or polyethylene glycols "Carbowaxes" (Registered Trade Mark) of suitable molecular weight.

The pharmaceutical compositions of this invention may contain, in addition to the active 4-arylpiperidine ingredient, one or more other physiologically active ingredients which elicit desirable complementary effects.

Examples of suitable pharmaceutical preparations according to the present invention are presented below for the purposes of facilitating a better understanding of this aspect of the invention.

Preparations

Preparation 1

For oral administration, sugar coated tablets may have the following composition, the tablets being made up in the usual manner.

| Ingredient | Amount (mg) |
|---|---|
| 1-(5-chloro-3-phenyl) indolinyl acetic acid piperidid | 100 |
| Lactose | 60 |
| Starch | 50 |
| Sugar | 75 |
| Talc | 5 |
| Gum Arabic | 5 |

Preparation 2

Capsules, made up in the usual manner may have the following composition:

| Ingredient | Amount (mg) |
|---|---|
| 3-Phenylindoline | 250 |
| Magnesium stearate | 5 |
| Lactose | 145 |

The present invention will be further described with reference to, but not limited by, the following specific examples.

EXAMPLE 1

3-Phenylindoline and the Monohydrochloride Thereof

A mixture of 50 g of 3-phenylindole, 500 ml of glacial acetic acid, 100 ml of boron trifluoride etherate and 100 g of zinc dust was heated to reflux and, under vigorous stirring, the low volatile components were continuously distilled off until the temperature reached 100° C. The reflux had continued for 90 minutes. After cooling, the reaction mixture was filtered to remove the zinc and zinc salts and the filter cake washed with ether. The filtrate was diluted with 500 ml of water and under cooling 200 ml of 50% aqueous sodium hydroxide was added dropwise. The organic layer was separated and the aqueous phase extracted with ether. The ether extracts were combined and washed with 125 ml 18% aqueous hydrochloric acid. The aqueous phase was basified with sodium hydroxide to pH 8-9 and extracted with ether. After removal of the solvent from the combined ether extracts, 30.1 g of dark oil was obtained which when distilled at 150° C/0.45 mm Hg gave 26.2 g of the desired 3-phenylindoline as a pale yellow viscous oil.

The monohydrochloride of 3-phenylindoline was found to have a melting point of 140°-1° C.

EXAMPLE 2

3-Phenylindoline 8.0 G of 3-phenylindole was dissolved in 120 ml of 96% ethanol and 60 ml of 48% hydrofluoroboric acid was added thereto. 0.4 G of platinum oxide was added to the mixture which was hydrogenated at 30 p.s.i. at room temperature for four hours. The catalyst was removed by filtration, the filtrate concentrated to ⅓ of the volume, basified with 50% aqueous sodium hydroxide and then extracted with ether. 6.7 G of a dark oil which was obtained from the ether extracts after removal of the solvent was chromatographed on silica gel to give 4.1 g of 3-phenylindoline as a pale yellow viscous oil.

EXAMPLE 3

3-Phenylindoline

A mixture of 4.0 g of 3-phenylindole, 80 ml of 86% ethanol, 35 ml of 48% hydrofluoroboric acid and 0.25 g of 10% Pd/C was hydrogenated at 60 p.s.i. and 60° C for 18 hours. The reaction mixture was worked up as in Example 2 and 1.9 g of pure 3-phenylindoline was obtained.

EXAMPLE 4

3-Phenylindoline 1.3 G of 3-phenylindole was suspended in 100 ml of 20% aqueous hydrochloric acid. The mixture was heated to 60° C while stirring vigorously and 20 g of zinc dust was added thereto in small portions over a period of 45 minutes. On completing the addition of zinc dust, the reaction mixture was heated to 100° C and maintained at this temperature for one hour, filtered hot, and the filtrate cooled to room temperature and washed with ether. The aqueous layer was basified with 50% aqueous sodium hydroxide and the desired product was extracted with ether and then purified by column chromatography using silica gel. The 3-phenylindoline was obtained in a yield of 0.8 g as a yellow viscous oil.

EXAMPLE 5

3-P-chlorophenylindoline

Using the same procedure as detailed in Example 1 3.5 g of 3-p-chlorophenylindole, 35 ml of glacial acetic acid, 7 ml of boron trifluoride etherate and 7 g of zinc dust were reacted together and the product worked up as in Example 1. In this way 1.5 g of the desired 3-p-chlorophenylindoline was obtained as a yellow oil.

EXAMPLE 6

N-acetyl-3-phenylindoline 1.0 G of 3-phenylindoline was dissolved in 10 ml of acetic anhydride at room temperature. After 10 minutes, the reaction mixture was poured into 100 ml of water, slightly basified with aqueous sodium hydroxide and extracted with methylene chloride. After removal of the methylenechloride, the residue was recrystallized from cyclohexane to give 1.15 g of the desired N-acetyl-3-phenylindoline which was found to have a 106°-7° C.

EXAMPLE 7

N-chloroacetyl-3-phenylindoline

A solution of 11.1 g of 3-phenylindoline in 60 ml of acetone was cooled to 0° C, 5.1 ml of chloroacetylchloride was added and the mixture poured into an ice cold solution of 10 g of sodium acetate in 50 ml of water. The mixture was then stirred for one hour at room temperature and the residual solid removed by filtration. Recrystallization from ethanol gave a yield of 13.0 g of the desired N-chloroacetyl-3-phenylindoline having a melting point of 76°-78° C.

EXAMPLE 8

N-chloracetyl-3-p-chlorophenylindoline

Using the procedure described in Example 7, 1.5 g of 3-p-chlorophenylindoline resulted in the production of 1.8 g of crude N-chloracetyl-3-chlorophenylindoline. Recrystallization of the crude product from ethanol gave 1.3 g of the desired pure product which was found to have a melting point of 97°-8° C.

EXAMPLE 9

N-acryloyl-3-phenylindoline

A mixture comprising 4.0 g of 3-phenylindoline, 40 ml of benzene, 5 ml of triethylamine and 4.0 g of acryloylchloride was stirred at 10°-15° C for 15 minutes. The mixture was then washed with water, the benzene solution dried and the solvent removed. 4.1 G of resin which was crystallized from ether to give 2.3 g of the desired N-acryloyl-3-phenylindoline which was found to have a melting point of 77°-8° C.

EXAMPLE 10

N-chloracetyl-3-phenyl-5-chloroindoline 2.7 G of N-chloracetyl-3-phenylindoline was added with vigorous stirring to a solution of 0.77 g of chlorine in 10 ml of glacial acetic acid which had been cooled to 15° C. The temperature of the mixture which rose to 33° C was cooled down to room temperature and the mixture stirred for a further hour. The resulting solution was poured into 100 ml of cold water. The liquid was decanted from the gummy residue, which was subsequently crystallized from ethanol to give 1.9 g of crystalline N-chloracetyl-3-phenyl-5-chloroindoline having a melting point of 107°-9° C.

EXAMPLE 11

N-(3-bromopropionyl)-3-phenylindoline

A solution of 9.1 ml of 3-bromopropionylchloride in 10 ml of dry benzene was added dropwise to a solution of 10.0 g of 3-phenylindoline and 10 ml of triethylamine in 100 ml of dry benzene cooled to 10° C. The precipitated triethylamine hydrochloride was separated by filtration, the benzene was removed from the filtrate in vacuo at room temperature and the residue recrystallized from ethanol to give 5.6 g of the desired N-(3-bromopropionyl)-3-phenylindoline having a melting point of 98°-9° C.

EXAMPLE 12

N-(2-bromopropionyl)-3-phenylindoline

A solution of 3.0 g of 2-bromopropionylchloride in 5 ml of benzene was added dropwise at 10° to a mixture of 3.0 g of 3-phenylindoline, 3.0 ml of triethylamine in 30 ml of dry benzene. The mixture was then washed with water, the benzene layer dried over sodium sulfate and the solvent removed in vacuo at room temperature to leave 4.9 g of the desired N-(2-bromopropionyl)-3-phenylindoline as a resin.

EXAMPLE 13

N-acetoacetyl-3-phenylinodoline

A solution of 2.0 g of diketene in 10 ml of dry benzene was added dropwise at 10°-15° C to a solution of 3.84 g of 3-phenylindolin in 35 ml of dry benzene. The solution was then stirred at room temperature for 90 minutes and the volatile components were removed in vacuo. The residue was recrystallized from ether to give 4.2 g of N-acetoacetyl-3-phenylindoline. A further recrystallization from ethanol gave a purer product having a melting point of 88°-9° C.

Analysis: $C_{18}H_{17}NO_2$(279.33) Calculated: C:77.39, H:6.13, N:5.01 Found: C:77.64, H:6.02, N:5.16

EXAMPLE 14

N-azidoacetyl-3-phenylindoline

A solution of 4.0 g of N-chloracetyl-3-phenylindoline and 1.1 g of sodium azide in 70 ml of 80% aqueous ethanol was refluxed for one hour. After cooling, the solution was diluted with 100 ml of water and extracted with methylene chloride. Evaporation of the solvent gave 2.8 g of the desired N-azidoacetyl-3-phenylindoline having a melting point of 72°-3° C.

EXAMPLE 15

N-aminoacetyl-3-phenylindoline

A mixture comprising 1.7 g of N-azidoacetyl-3-phenylindoline dissolved in 60 ml of methylalcohol and 0.5 of 5% Pd/C was hydrogenated at 50 lb/sq. in. at room temperature for 16 hours. The catalyst was filtered off and the solvent removed to give a colorless resin which was converted into 1.5 g of crystalline hydrochloride using ethanolic hydrochloric acid in the usual manner. Recrystallization from ethanol gave pure hydrochloride which was found to have a melting point of 259°-60° C.

Analysis: $C_{16}H_{17}N_2OCl$(288.78) Calculated: C:66.54, H:5.935, N:9.70, Cl:12.23 Found: C:66.42, H:5.96, N:9.45, Cl:11.95

EXAMPLE 16

N-dimethylaminoacetyl-3-phenylindoline 2.0 G of N-chloracetyl-3-phenylindoline was added to a saturated solution of dimethylamine in 50 ml of dry benzene. The mixture was stirred for one hour, the dimethylamine hydrochloride filtered off and the filtrate evaporated to dryness leaving 2.1 g of a white crystalline residue m.p. 101°-103° C. The residue was converted into N-dimethylaminoacetyl-3-phenylindoline hydrochloride by treatment with methanolic hydrochloric acid in the usual manner. The N-dimethylaminoacetyl-3-phenylindoline hydrochloride has a melting point of 235°-43° C.

Analysis: $C_{18}H_{21}ClN_2O$(316.83) Calculated: C:68.23, H:6.68, N:8.84, Cl:11.19 Found: C:68.12, H:6.21, N:8.70, Cl:11.00

EXAMPLE 17

N-[1-(4-methylpiperazino)acetyl]-3-phenylindoline

A mixture of 1.2 g of N-methylpiperazine and 3.0 g of N-chloracetyl-3-phenylindoline in 30 ml of benzene was refluxed for 2½ hours. After cooling, the resulting precipitate was removed by filtration. After drying the yield of crude N-[-1-(4-methylpiperazino)acetyl]-3-phenylindoline melting at 214°-217° C was 3.0 g. Recrystallization from ethanol gave pure N-[1-(4-methylpiperazino)acetyl]-3-phenylindoline and has a melting point of 229°-230° C.

Analysis: $C_{21}N_{16}N_3ClO$(371.90) Calculated: C:67.81, H:7.04, N:11.298, Cl:9.53 Found: C:67.56, H:7.10, N:11.19, Cl:9.83

EXAMPLE 18

N-(3,3-dimethylacryloyl)-3-phenylindoline

The procedure of Example 16 was repeated using 1.95 g of 3-phenylindoline and 1.5 g of 3,3-dimethylacryloyl chloride. In this way 1.6 g of the desired N-(3,3-dimethylacryloyl)-3-phenylindoline having a melting point of 97°-8° C was obtained.

EXAMPLE 19

N-(2-methylamino)propionyl-3-phenylindoline

A solution comprising 3.0 g of N-(2-bromopropionyl)-3-phenyl indoline in 30 ml of benzene was saturated with methylamine. The solution was then stirred for 16 hours at room temperature and then washed with water. The residue, after removing the solvent, was treated with methanolic HCl is known manner and the so-obtained solid recrystallized from isopropylalcohol to give 1.6 g of the desired N-(2-methylamino)-propionyl-3-phenylindoline hydrochloride which was found to have a melting point of 218°-9° C.

Analysis: $C_{18}H_{21}ClN_2O$ (316.83) Calculated: C:68.23, H:6.68, N:8.84 Found: C:68.28, H: 6.84 N:8.25

EXAMPLE 20

N-(3-dimethylamino)-propionyl-3-phenylindoline 1.0 G of N-(3-bromopropionyl)-3-phenylindoline in 60 ml of 65% aqueous ethanol was heated to 50° C and gaseous dimethylamine was continuously passed into the solution for one hour. 75 Ml of water was added to the solution and the mixture extracted with benzene. Upon removal of the solvent 0.8 g of resin was obtained which was converted into 0.8 g of crystalline N-(3-dimethylamino)propionyl-3-phenylindoline. The hydrochloride with methanolic HCl by treatment in known ways with hydrochloride when recrystallized from ethanol was found to have a melting point of 223°-4° C.

EXAMPLE 21

N-carbamoyl-3-phenyl indoline

A mixture comprising 2.3 g of 3-phenyl indoline hydrochloride in 23 ml of water and 0.81 g of potassium isocyanate in 23 ml of ethanol was stirred for 15 minutes at room temperature. The precipitate which resulted was filtered off, washed with water and recrystallized from dilute ethanol. The yield of N-carbamoyl-3-phenylindoline was 0.9 g and the product had a melting point of 144°-145° C.

EXAMPLE 22

N,N-dimethyl-[1-(3-phenyl-5-chloro-indolinyl)]-acetamide

To a solution of 2.3 g of 3-phenyl-5-chloroindoline in 30 ml of benzene, 3 ml of triethylamine and 1.8 g of N,N-dimethyl bromacetamide were added and the reaction mixture refluxed for four hours. The precipitate of triethylamide which resulted was filtered off and the filtrate evaporated to dryness. The oily residue became crystalline after treatment with ether. The yield after recrystallization from ethanol was 1.25 g and the product had a melting point of 119°-120° C.

EXAMPLE 23

2', 6'-Dichloro-2-[1-(3-phenylindolinyl)]-acetanilide

A mixture of 2.0 g of 3-phenylindoline, 2.4 g of 2',6'-dichloro-2-chloroacetanilide and 1.5 ml of triethylamine in 20 ml of benzene was refluxed overnight. The reaction mixture was filtered, washed with brine and dried over sodium sulfate. Evaporation of the benzene solvent gave 1.8 g of the desired product in the form of crystals which after recrystallization from ethanol-water melted at 159°-160° C.

EXAMPLE 24

1-(5-Chloro-3-phenyl)indolinyl acetic acid piperidid

A mixture of 2.3 g of 5-chloro-3-phenyl indoline dissolved in 30 ml of benzene, 2 ml of triethylamine and 2.2 g of N-hexamethyleno-bromacetamide was refluxed for one hour, cooled, diluted with ether, washed with water and finally dried over sodium sulfate. The residue after evaporation of solvents became crystalline upon treatment with ether and was recrystallized from ethanol to give 1.3 g of desired product. The melting point of an analysis sampel was 119°-120° C.

Elemental Analysis: $C_{22}H_{25}N_2Cl_0$ Calculation: C:71.16%, H:6.83%, N:7.6%, Cl:9.61% Found: C:70.90%, H:6.95%, N:7.80%; Cl:9.34%

EXAMPLE 25

N-(2-piperidinoethyl)-3-phenyl-indoline

A mixture was prepared by adding 3.0 g of N-pentamethyleno-[1-(3-phenyl indolinyl)]acetamide (prepared in a manner analogous to that of Example 24) a slurry of 0.4 g of lithium aluminum hydride in 60 ml of anhydrous tetrahydrofurane. This reaction mixture was refluxed for one hour after which time the starting material was virtually eliminated. After work up in usual manner, 2.0 g of crude N-(2-piperidinoethyl)-3-phenyl indoline was obtained as an oil which was converted into a crystalline hydrochloride. The melting point of the latter when recrystallized from ethanol/ether was 184°-185° C, and 1.3 g was obtained.

Using the general procedures described in detail in the foregoing Examples with, of course, the appropriate choice of starting materials the compounds of the following restricted formula I were prepared. The substituent $R_2$ in the formula is in the para position unless stated otherwise. For those compounds containing basic nitrogen, the melting point of the corresponding hydrochloride is given unless othewise stated.

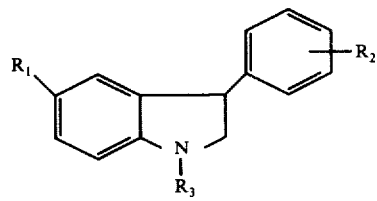

| Example No. | $R_1$ | $R_2$ | $R_3$ | Melting Point |
|---|---|---|---|---|
| 26 | F | F | H | 135-137° C |
| 27 | CH$_3$O | Cl | H | 203-205° C |
| 28 | H | m-F | H | 132-135° C |
| 29 | Br | H | —CO—CH$_2$Cl | 121-123° C |
| 30 | Cl | H | —C(=O)—CH$_3$ | 119-120° C |
| 31 | Cl | H | —COCH$_2$CH$_2$—Br | 95-97° C |
| 32 | H | H | —COCH=CH—CH$_3$ | 92-94° C |
| 33 | Cl | H | —COCH=CH—CH$_3$ | 124-125° C |
| 34 | Cl | H | —CONH$_2$ | 152-154° C |
| 35 | H | H | —CO—CH$_2$NH—CH$_3$ | 266-268° C |
| 36 | H | H | —CO—CH$_2$NH—CH(CH$_3$)$_2$ | 284-285° C |
| 37 | H | H | —CO—CH$_2$—NH—$_n$C$_4$H$_9$ | 224-225° C |
| 38 | H | H | —CO—CH$_2$—NH-(2-pyridyl) | 210-211° C |
| 39 | H | H | —CO—CH$_2$N(CH$_3$)$_2$ | 243-246° C |
| 40 | Br | H | —CO—CH$_2$N(CH$_3$)$_2$ | 250-253° C |
| 41 | H | H | —CO—CH(CH$_3$)—NH—CH—CH(CH$_3$)$_2$ | 263-263° C |
| 42 | H | H | —CO—CH(CH$_3$)—N(CH$_3$)$_2$ | 240-241° C |

-continued

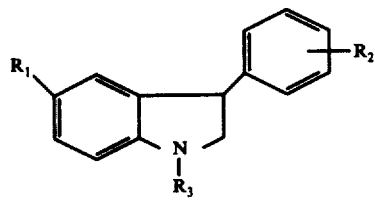

| Example No. | R₁ | R₂ | R₃ | Melting Point |
|---|---|---|---|---|
| 43 | H | H | —COCH₂CH₂NH—CH(CH₃)₂ | 173–174° C |
| 44 | H | H | —COCH(CH₃)—NH—CH(CH₃)₂ | 240–241° C |
| 45 | Cl | H | —COCH₂NH—CH₃ | 285° (d) |
| 46 | H | H | —COCH₂N(C₂H₅)₂ | 68–69° C (base) |
| 47 | Cl | H | —COCH₂CH₂—NH—CH(CH₃)₂ | 199–200° C |
| 48 | Cl | H | —COCH₂CH₂NH—CH₃ | 224–225° C |
| 49 | Cl | H | —CO—CH(CH₃)—NH—CH(CH₃)₂ | 242–244° C |
| 50 | H | H | —COCH₂—CH(CH₃)—NH—CH₃ | 156–158° C |
| 51 | H | H | —CO—CH₂—CH(CH₃)—NH—CH₂CH₃ | 153–155° C |
| 52 | H | H | —CO—CH₂—CH(CH₃)—N(CH₃)₂ | 197° C |
| 53 | H | H | —CO—CH₂—CH(CH₃)—NH—CH(CH₃)₂ | 191° C |
| 54 | Cl | H | —CO—CH₂—CH(CH₃)—N(CH₃)₂ | 183–185° C (d) |
| 55 | Cl | H | —CO—CH₂—CH(CH₃)—NH—CH₃ | 185° C |
| 56 | Cl | H | —CO—CH₂—CH(CH₃)—NH—CH₂CH₃ | 175–177° C |
| 57 | Cl | H | —CO—CH(CH₃)—NH—CH₃ | 134–135° C |
| 58 | CH₃O | Cl | —COCH₂CH₂N(CH₃)₂ | 229–230° C |
| 59 | CH₃O | Cl | —CH₂—CONH—(2,6-(CH₃)₂C₆H₃) | 173–175° C |
| 60 | F | H | —COCH₂N(CH₃)₂ | 238° C |
| 61 | F | H | —COCH₂N(CH₃)₂ | 239–240° C |
| 62 | F | F | —CH₂CONH—(2,6-(CH₃)₂C₆H₃) | 161–162° C |

-continued

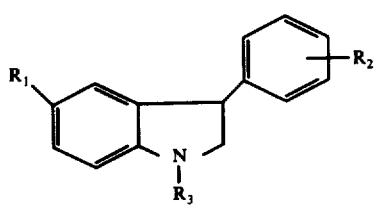

| Example No. | $R_1$ | $R_2$ | $R_3$ | Melting Point |
|---|---|---|---|---|
| 63 | H | H | —CO—CH$_2$N(morpholine) | 234–236° C |
| 64 | H | H | —CO—CH$_2$N(piperidine) | 208–210° C |
| 65 | H | H | —CO—CH$_2$N(pyrrolidine) | 230–231° C |
| 66 | H | H | —CO—CH$_2$N(piperidine) | 179–180° C |
| 67 | H | H | —CO—CH(CH$_3$)—N(morpholine) | 244–245° C |
| 68 | H | H | —COCH$_2$CH$_2$N(morpholine) | 239–240° C |
| 69 | H | H | —COCH$_2$CH$_2$N(piperidine) | 237–238° C |
| 70 | Cl | H | —COCH$_2$N(pyrrolidine) | 260–261° C |
| 71 | Cl | H | —COCH$_2$—N(morpholine) | 239–240° C |
| 72 | Cl | H | —COCH$_2$CH$_2$N(pyrrolidine) | 244–245° C |
| 73 | H | H | —CO—CH$_2$—CH(CH$_3$)—N(morpholine) | 169° C (d) |
| 74 | Cl | H | —CO—CH(CH$_3$)—N(pyrrolidine) | 220–222° C |
| 75 | H | H | —CH$_2$CON(CH$_3$)$_2$ | 69–70° C |

-continued

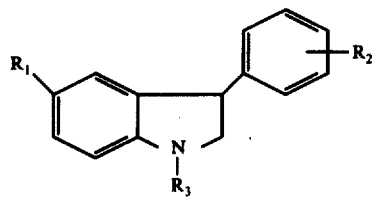

| Example No. | $R_1$ | $R_2$ | $R_3$ | Melting Point |
|---|---|---|---|---|
| 76 | Cl | H | —CH₂—CO—NH—(2,6-dimethylphenyl) | 140–141° C |
| 77 | Cl | H | CH₂CONH—CH(CH₃)₂ | 102–103° C |
| 78 | Cl | H | CH₂CONH—C(CH₃)₃ | 116–117° C |
| 79 | H | H | CH₂CONH—C(CH₃)₃ | 75–76° C |
| 80 | Cl | H | CH₂CONH—CH₃ | 118° C |
| 81 | H | H | —CH₂CONH—(2,6-dichlorophenyl) | 159–160° C |
| 82 | Cl | H | CH₂CONH—(2,6-dichlorophenyl) | 175° C |
| 83 | H | H | —CH₂CON(morpholino) | 135–138° C |
| 84 | Cl | H | CH₂CON(piperidino) | 119–120° C |
| 85 | Cl | H | CH₂CON(pyrrolidino) | 145–146° C |
| 86 | Cl | H | CH₂CON(morpholino) | 159–160° C |
| 87 | H | H | —CH(CH₃)—CO—N(piperidino) | 164–165° C |

Further compounds according to the present invention are as follows:

| | | | |
|---|---|---|---|
| 88 | 6-Cl | m-OCH₃ | H |
| 89 | 6-Br | m-CH₃ | H |
| 90 | 5-CH₃ | m-Cl | H |
| 91 | 5-OC₂H₅ | o-CH₃ | H |
| 92 | 5-OCH₃ | o-C₂H₅ | H |
| 93 | 7-Cl | H | H |
| 94 | 7-Br | p-Cl | H |
| 95 | 7-Cl | p-CH₃ | H |
| 96 | 5-CH₂CH₃ | p-Br | H |
| 97 | 6-CH₃ | H | H |
| 98 | 5-Cl | p-F | —C₃H₆—NH₂ |
| 99 | H | H | —C₃H₆—NHCH₃ |
| 100 | 6-Br | H | —C₂H₄—N(CH₃)₂ |
| 101 | H | m-Cl | C₄H₈NH₂ |
| 102 | 7-Cl | p-Br | —C₂H₄—NHC₂H₅ |
| 103 | 5-Cl | H | C₄H₈—N⟨piperidine⟩ |
| 104 | H | H | C₂H₄—N⟨piperazine⟩NH |
| 105 | 5-CH₃ | p-Cl | —C₂H₄—N⟨piperazine⟩N—CH₃ |
| 106 | 5-Cl | H | —C₂H₄—NH-(2-pyridyl) |
| 107 | 5-Cl | p-Cl | —C(=O)—C₂H₄N₃ |

We claim:

1. A 3-phenylindoline of the formula Ie:

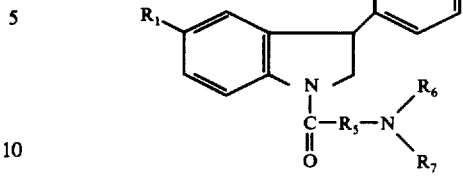

wherein $R_1$ is hydrogen or halogen; $R_5$ is a straight or branched chain lower alkylene; and one of $R_6$ and $R_7$ is hydrogen and the other is lower alkyl, or both $R_6$ and $R_7$ are lower alkyl; or a pharmaceutically acceptable addition salt thereof obtained from an inorganic or organic acid.

2. A 3-phenylindoline as claimed in claim 1 which is N-(2-dimethylaminoacetyl)-3-phenylindoline or a pharmaceutically acceptable addition salt thereof obtained from an inorganic or organic acid.

3. A 3-phenylindoline as claimed in claim 1 which is N-(2-dimethylamino)-propionyl-3-phenylindoline or a pharmaceutically acceptable addition salt thereof obtained from an inorganic or organic acid.

4. A 3-phenylindoline as claimed in claim 1 which is N-(2-methylamino)-propionyl-3-phenyl-5-chloroindoline or a pharmaceutically acceptable addition salt thereof obtained from an inorganic or organic acid.

5. A 3-phenylindoline as claimed in claim 1 which is N-(3-dimethylamino)-propionyl-3-phenylindoline or a pharmaceutically acceptable addition salt thereof obtained from an inorganic or organic acid.

6. A 3-phenylindoline as claimed in claim 1 which is N-(2-dimethylaminoacetyl)-3-phenyl-5-fluoroindoline or a pharmaceutically acceptable addition salt thereof obtained from an inorganic or organic acid.

* * * * *